United States Patent [19]

Haupt

[11] Patent Number: 4,685,927

[45] Date of Patent: Aug. 11, 1987

[54] BRAKED KNEE JOINT

[75] Inventor: Werner Haupt, Duderstradt-Tiftlingerode, Fed. Rep. of Germany

[73] Assignee: Otto Bock Orthopaedische Industrie Besitz- und Verwaltungs-Komanditgesellschaft, Duderstadt, Fed. Rep. of Germany

[21] Appl. No.: 867,730

[22] Filed: May 28, 1986

[30] Foreign Application Priority Data

May 28, 1985 [DE] Fed. Rep. of Germany ....... 3519046

[51] Int. Cl.$^4$ ............................................... A61F 2/64
[52] U.S. Cl. ......................................... 623/44; 623/46
[58] Field of Search .................................. 623/43–46, 623/39, 40

[56] References Cited

U.S. PATENT DOCUMENTS 2,400,032  5/1946  Talbot .................................... 623/44
2,853,712  9/1958  Bach ..................................... 623/44

FOREIGN PATENT DOCUMENTS 243431   11/1965  Austria .
661128    1/1932  Fed. Rep. of Germany .
843880    5/1952  Fed. Rep. of Germany .
1566352   7/1970  Fed. Rep. of Germany ........ 623/44
1491233  10/1974  Fed. Rep. of Germany .
8515631   8/1985  Fed. Rep. of Germany .
1297833   5/1962  France ................................... 623/44
1449998   7/1966  France ................................... 623/44
1033949   6/1966  United Kingdom ................. 623/44

Primary Examiner—Ronald L. Frinks
Attorney, Agent, or Firm—Schwartz, Jeffery, Schwaab, Mack, Blumenthal & Evans

[57] ABSTRACT

A braked knee joint having a thigh part and a lower leg part which are provided with braking surfaces adapted to one another and which, because of the capacity for axial movement of the thigh part relative to the lower leg part, are pressed against one another during loading. The braking surfaces essentially have a contour which is circular in vertical section and which has a constant radius relative to the rotational axis. The joint includes a suitable stop to produce a jerk-free termination of the extension movement of the knee joint out of the flexed position. The stop is formed by providing the braking surface of the thigh part with a front end piece which is at a distance which increases from the rotational axis and is greater than the constant radius, and by providing a corresponding front end piece of the braking surface of the lower leg part so that, with increasing extension of the knee joint in the unloaded condition, a constantly increasing area of the braking surfaces comes into frictional contact and this forms the stop.

3 Claims, 3 Drawing Figures

BRAKED KNEE JOINT

BACKGROUND OF THE INVENTION

The present invention relates to a braked knee joint having a thigh part and a lower leg part which are provided with braking surfaces which are adapted to one another and which, because of the moving capacity of the thigh part relative to the lower leg part, are pressed against one another during loading. The braking surfaces essentially have a contour which is circular in vertical section and has a constant radius relative to the axis of rotation. The braked knee joint also has a stop for limiting the extending movement of the knee joint out of the flexed position.

A braked knee joint of this general type is known, for example, from Austrian Pat. No. 243,431. When the knee joint is loaded, for example, when walking, the braking surfaces press heavily against one another and, because of the frictional force which exists between them, they brake the movement of the knee joint. When the knee joint is fully loaded in the extended position, the braking surfaces virtually provide an arresting effect which is released only by relieving the load on the joint.

In a braked knee joint of this type, the lower leg, when the load is relieved, can virtually swing freely relative to the thigh, because the braking surfaces produce practically no frictional force. When the thigh is brought forward during the walking action, the lower leg, assisted by an advancing spring, follows in a swinging movement until the leg is extended. This forward swinging movement of the lower leg is limited by a stop. Despite greater efforts in the designing of the stop, success has not been achieved in constructing a stop which leads to a gentle stop movement for all applications in which the forward swinging of the lower leg part takes place with a more or less large swing. Heretofore, a jerky, abrupt termination of the forward swinging movement could therefore not be avoided.

SUMMARY OF THE INVENTION

It is therefore an object of the present invention to provide an improved braked knee joint. In particular, it is an object of the invention to provide a braked knee joint of the type mentioned at the outset in which a jerky termination of the forward swinging movement of the lower leg can be reliably avoided, even when the swinging momentum varies considerably.

In accomplishing the following objects, there has been provided according to the present invention a braked knee joint, comprising a thigh member; a lower leg member rotatably articulated to the thigh member to form a knee joint capable of rotating about an axis of rotation between a flexed orientation of the members and an extended position of the members; means for permitting axial movement of the members with respect to one another; a first braking surface at the lower end of the thigh member and a second braking surface at the upper end of the lower leg member, the braking surfaces having a generally circular contour and a constant radius of curvature with respect to the axis of rotation, the braking surfaces being adapted for frictional interengagement upon axial loading of the knee joint; and means for gradually stopping rotational movement of the knee joint upon reaching the extended position, comprising means associated with the first and second braking surfaces for gradually increasing frictional engagement of the members as the extended position is approached. Preferably, the means for gradually increasing frictional engagement comprises first and second front end pieces located adjacent to the first and second braking surfaces, these front end pieces each having a contour which extends at an increasing distance from the axis of rotation, the distance being greater than the radius of curvature, whereby the front end pieces provide an increasing area of frictional engagement as the extended position is approached.

Further objects, features and advantages of the present invention will become apparent from the detailed description of preferred embodiments which follows, when considered together with the attached figures of drawing.

BRIEF DESCRIPTION OF THE DRAWINGS

The invention is described in greater detail below with reference to exemplary embodiments shown in the drawings, in which.

DETAILED DESCRIPTION OF THE PREFERRED EMBODIMENTS

According to the invention, the braking surface of the thigh part has a front end piece which is at a larger and an increasing distance from the rotational axis, relative to the constant radius, and the front end piece of the braking surface of the lower leg part is correspondingly adapted, so that, with increasing extension of the knee joint in the unloaded condition, a constantly increasing area of the braking surfaces comes into frictional contact and thus forms the stop.

According to the invention, the stop is thus formed not by a separate part but by a skillful design of the braking surfaces. As a result of the braking surface end pieces developed according to the invention, an increasing area of the opposing braking surfaces rubs together just before the final extension of the knee joint, and therefore the extending movement is braked with an increasing braking force. At the same time, advantage is taken of the fact that the braking surfaces, in the normal function of the knee, are suitable for braking in the loaded condition, so that they are also suitable for braking in the unloaded condition just before the complete extension of the knee joint is reached. The normal function of the knee joint when flexing and then extending again is not affected by the end pieces, because a distinct gap develops between the braking surfaces in the area of the end pieces during flexing, so that the braking surfaces do not participate in the function of the braked knee joint during these movement stages.

The braked knee joint according to the invention can be put into effect most expediently if the braking surfaces are formed by plane strips perpendicular to the direction of curvature. This design readily permits the appearance of the knee joint to be improved, which can be a problem in the case of wedge-shaped braking surfaces.

Figure 1:
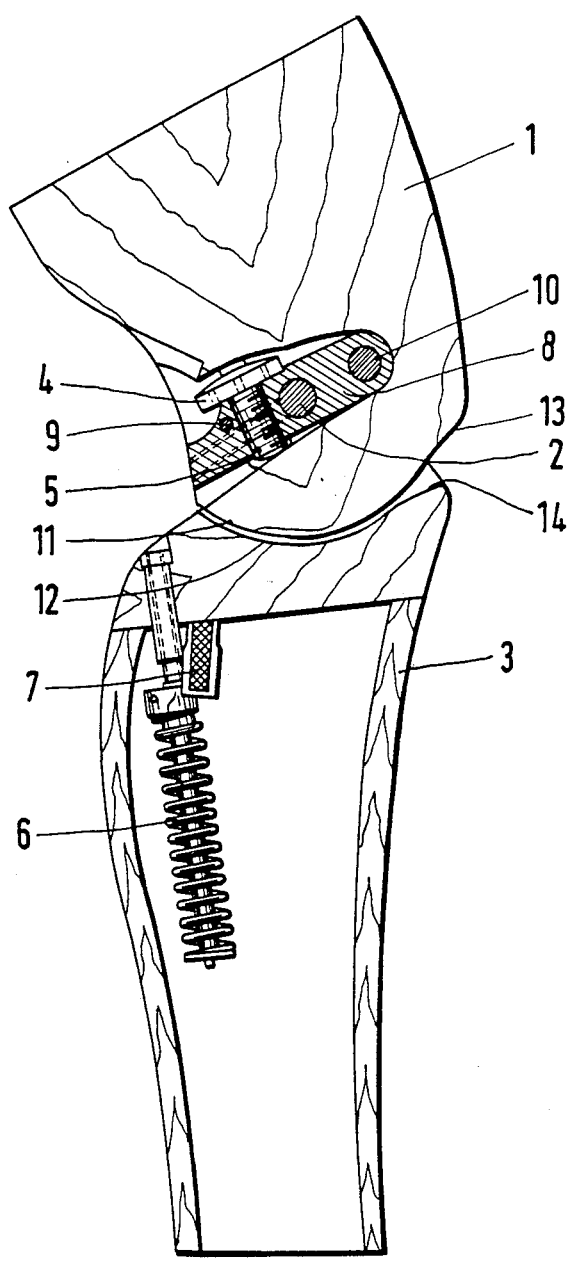
FIG. 1 is a lateral cross-sectional view showing the braked knee joint according to the invention in a flexed position.
Figure 2:
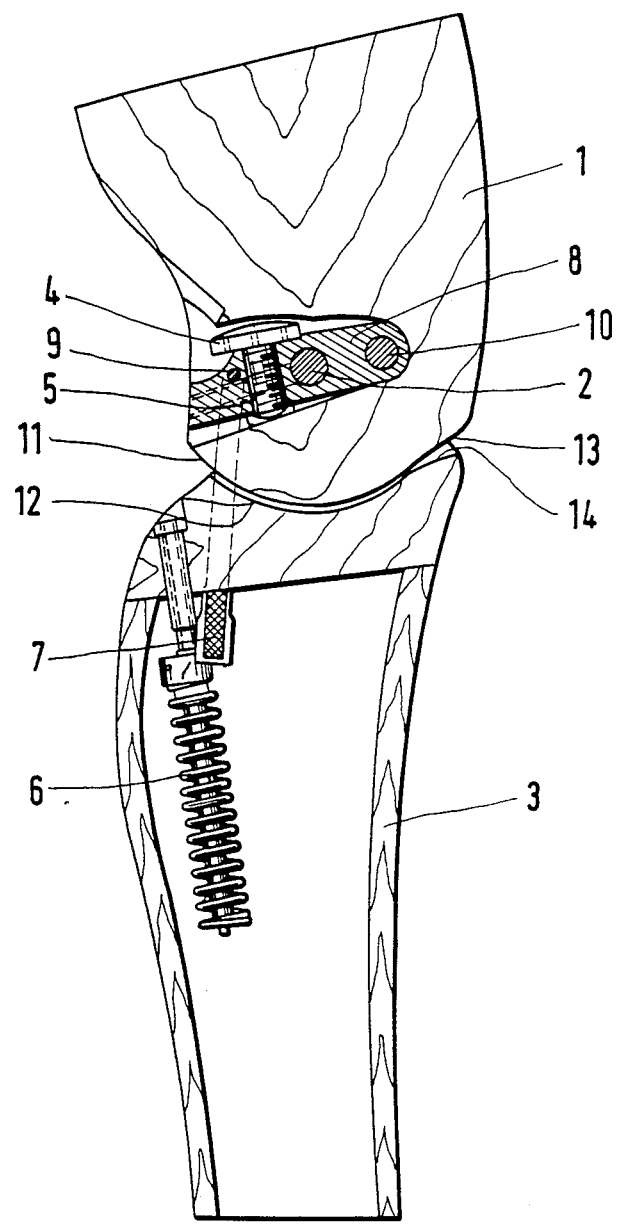
FIG. 2 is a view similar to FIG. 1 showing the braked knee joint according to the invention in a position just before the complete extension of the knee joint.
Figure 3:
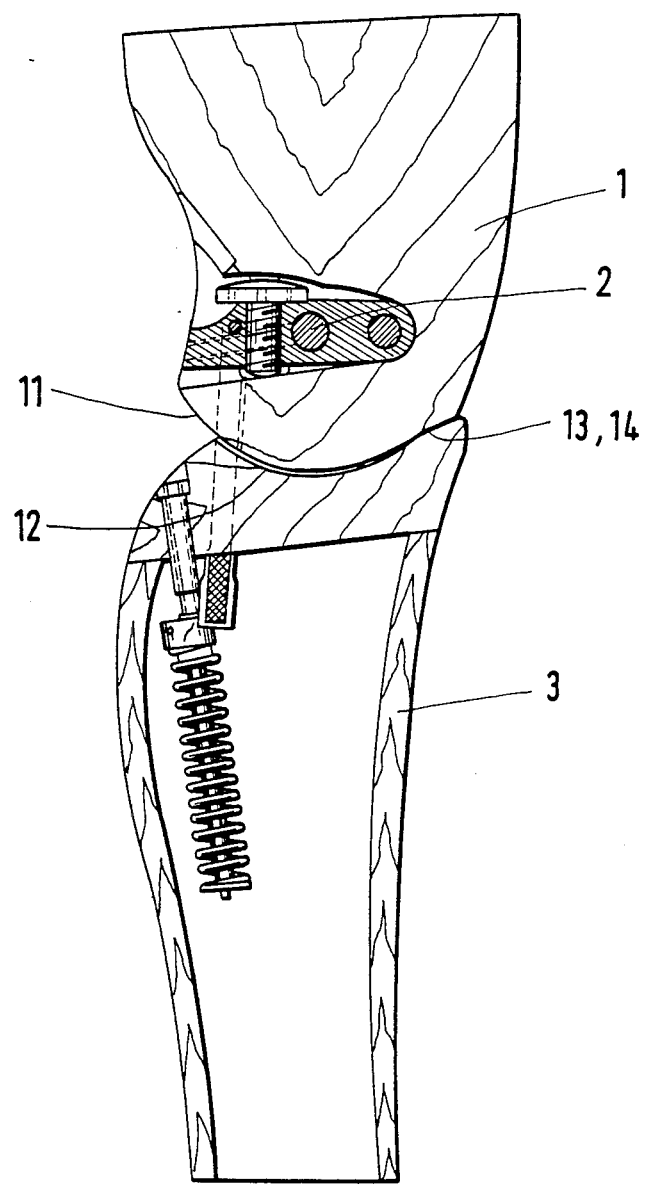
FIG. 3 is a view similar to FIGS. 1 and 2 showing the braked knee joint according to the invention when completely extended.

FIGS. 1-3 show the braked knee joint according to the invention, in each case in a vertical sectional representation. The knee joint consists of a thigh 1 which is connected to a lower leg part 3 via a rotational axis 2. For this purpose, the lower leg part 3 has extensions which are bent laterally upwardly and laterally enclose the thigh part 1 up to the axis 2, so that the rotatable connection between the thigh part 1 and the lower leg part 3 can take place at the level of the axis 2. The thigh part 1 embraces the rotational axis 2 with a slotted hole, so that the lower leg part 3 is vertically movable to a certain extent relative to the thigh part 1. This vertical distance can be set by a lift adjuster 4 into which a restoring spring 5 is integrated. A recuperator spring 6, arranged in the hollow lower leg part 3, is connected to recuperator guides 7 which are articulated about a rotational axis 9 in a swinging block 8 in the thigh part 1. The swinging block 8 is firmly connected to the thigh part 1 at the inner end of the swinging block 8 by means of pins 10.

For developing a braking function, the thigh part 1 and the lower leg part 3 are in each case provided with a braking surface 11 and 12 which are formed by plane strips which, in vertical section, are bent essentially in a circular shape at a constant radius from the axis 2. At the front end, the braking surfaces 11 and 12 are provided with end pieces 13 and 14 which run out forward at an increasing distance from the axis 2.

In the slightly flexed position of the knee joint (relieved of the load), shown in FIG. 1, the braking surfaces 11 and 12, although in light contact with one another in the area of the constant radius, do not exert any substantial frictional force on account of their sliding properties, The end pieces 13 and 14 are separated from one another by a wedge-shaped intermediate space. When the lower leg part 3 swings forward, it rotates forward about the axis 2. FIG. 2 shows a position in which the front end pieces 13 and 14 of the braking surfaces 11 and 12, directly adjoining the parts with a constant radius, come into contact with one another and in so doing exert a certain frictional force. When the knee is extended further, this common contact area between the two end pieces 13 and 14 increases, so that a constantly increasing frictional force is set up against further rotational movement of the lower leg part 3 about the axis 2 in the thigh part 1, because the end pieces 13 and 14 rub on one another during the rotational movement.

FIG. 3 shows the fully extended position in which the end pieces 13 and 14 lie on one another completely under pressure, without requiring any loading on the knee joint to produce this condition.

The end pieces 13 and 14 therefore produce a braking force which increases with increasing degree of extension when the lower part 3 swings forward relative to the thigh part 1, as a result of which the gentle braking of the lower leg part 3 is achieved. At the same time, gentle braking is achieved during both a pronounced forward swing and a weak forward swing.

The braking surfaces 11 and 12 are preferably made as plane strips perpendicular to the direction of curvature. The strip 11 on the thigh part preferably consists of vulcanized fiber and the strip 12 on the lower leg part is preferably formed by a silicone-coated fabric belt.

What is claimed is:

1. A braked knee joint, comprising:
   a thigh member;
   a lower leg member rotatably articulated to said thigh member to form a knee joint capable of rotating about an axis of rotation between a flexed orientation of said members and an extended position of said members;
   means for permitting axial movement of said members with respect to one another;
   a first braking surface at the lower end of said thigh member and a second braking surface at the upper end of said lower leg member, said braking surfaces having a generally circular contour and a constant radius of curvature with respect to said axis of rotation, said braking surfaces being adapted for frictional interengagement upon axial loading of the knee joint; and
   means for gradually stopping rotational movement of the knee joint upon reaching said extended position, said stopping means comprising means associated with said first and second braking surfaces for gradually increasing frictional engagement of said members as said extended position is approached, wherein said means for gradually increasing frictional engagement comprises first and second front end pieces located adjacent to said first and second braking surfaces, said front end pieces each having a contour which extends at an increasing distance from said axis of rotation, said distance being greater than said radius of curvature, whereby said front end pieces provide an increasing area of frictional engagement as said extended position is approached.

2. A braked knee joint as claimed in claim 1, wherein said first and second braking surfaces comprise planar strips arranged perpendicular to the direction of curvature.

3. A braked knee joint as claimed in claim 1, wherein said means for permitting axial movement comprises means for movably mounting said axis of rotation in said thigh member.

* * * * *